(12) United States Patent
Pollack et al.

(10) Patent No.: US 7,320,693 B2
(45) Date of Patent: Jan. 22, 2008

(54) METHODS AND INSTRUMENTS FOR CLOSING LAPAROSCOPIC TROCAR PUNCTURE WOUNDS

(76) Inventors: Stanley B. Pollack, 71 Forest Ave., Nesconset, NY (US) 11767; Anthony D. Costabile, P.O. Box 2097, Setauket, NY (US) 11733

( * ) Notice: Subject to any disclaimer, the term of this patent is extended or adjusted under 35 U.S.C. 154(b) by 854 days.

(21) Appl. No.: 10/645,405

(22) Filed: Aug. 21, 2003

(65) Prior Publication Data

US 2005/0043746 A1    Feb. 24, 2005

(51) Int. Cl.
A61B 17/04    (2006.01)
(52) U.S. Cl. ..................................... 606/144
(58) Field of Classification Search ........ 606/144–148, 606/150, 215, 221, 220, 232, 139, 213; 289/10, 289/17
See application file for complete search history.

(56) References Cited

U.S. PATENT DOCUMENTS

| | | | |
|---|---|---|---|
| 4,779,616 A | 10/1988 | Johnson | |
| 5,195,505 A | 3/1993 | Josefsen | |
| 5,330,488 A | 7/1994 | Goldrath | |
| 5,364,410 A | 11/1994 | Failla et al. | |
| 5,391,182 A | 2/1995 | Chin | |
| 5,437,681 A | 8/1995 | Meade et al. | |
| 5,439,469 A | 8/1995 | Heaven et al. | |
| 5,462,560 A | 10/1995 | Stevens | |
| 5,474,568 A | 12/1995 | Scott | |
| 5,476,470 A | 12/1995 | Fitzgibbons, Jr. | |
| 5,503,634 A | 4/1996 | Christy | |
| 5,562,688 A | 10/1996 | Riza | |
| 5,591,180 A | 1/1997 | Hinchliffe | |
| 5,697,889 A | 12/1997 | Slotman et al. | |
| 5,716,369 A | 2/1998 | Riza | |
| 5,722,981 A * | 3/1998 | Stevens | 606/148 |
| 5,741,277 A | 4/1998 | Gordon et al. | |
| 5,830,232 A | 11/1998 | Hasson | |
| 5,836,956 A | 11/1998 | Buelna et al. | |
| 5,954,734 A * | 9/1999 | Thomason et al. | 606/148 |
| 5,984,948 A * | 11/1999 | Hasson | 606/213 |
| 5,993,466 A | 11/1999 | Yoon | |
| 6,152,936 A | 11/2000 | Christy et al. | |
| 6,245,080 B1 * | 6/2001 | Levinson | 606/144 |

* cited by examiner

Primary Examiner—Anhtuan T. Nguyen
Assistant Examiner—Tuan Van Nguyen
(74) Attorney, Agent, or Firm—Galgano & Associates, PLLC

(57) ABSTRACT

An instrument for applying a suture to a trocar wound includes an obturator coupled to a central shaft and a coaxially disposed skin pressure plate. The obturator and skin pressure plate are movable relative to each other, and function together to position the tissue and needles relative to each other. The skin pressure plate is provided with two spaced apart needle guides. A pair of hollow needles, held in the guides of the pressure plate are coupled to a needle mounting plate which is movable over the central shaft. One of the needles is provided with a suture control mechanism for moving a suture through the needle and the other needle is provided with a snare control mechanism for moving a snare through the needle.

7 Claims, 6 Drawing Sheets

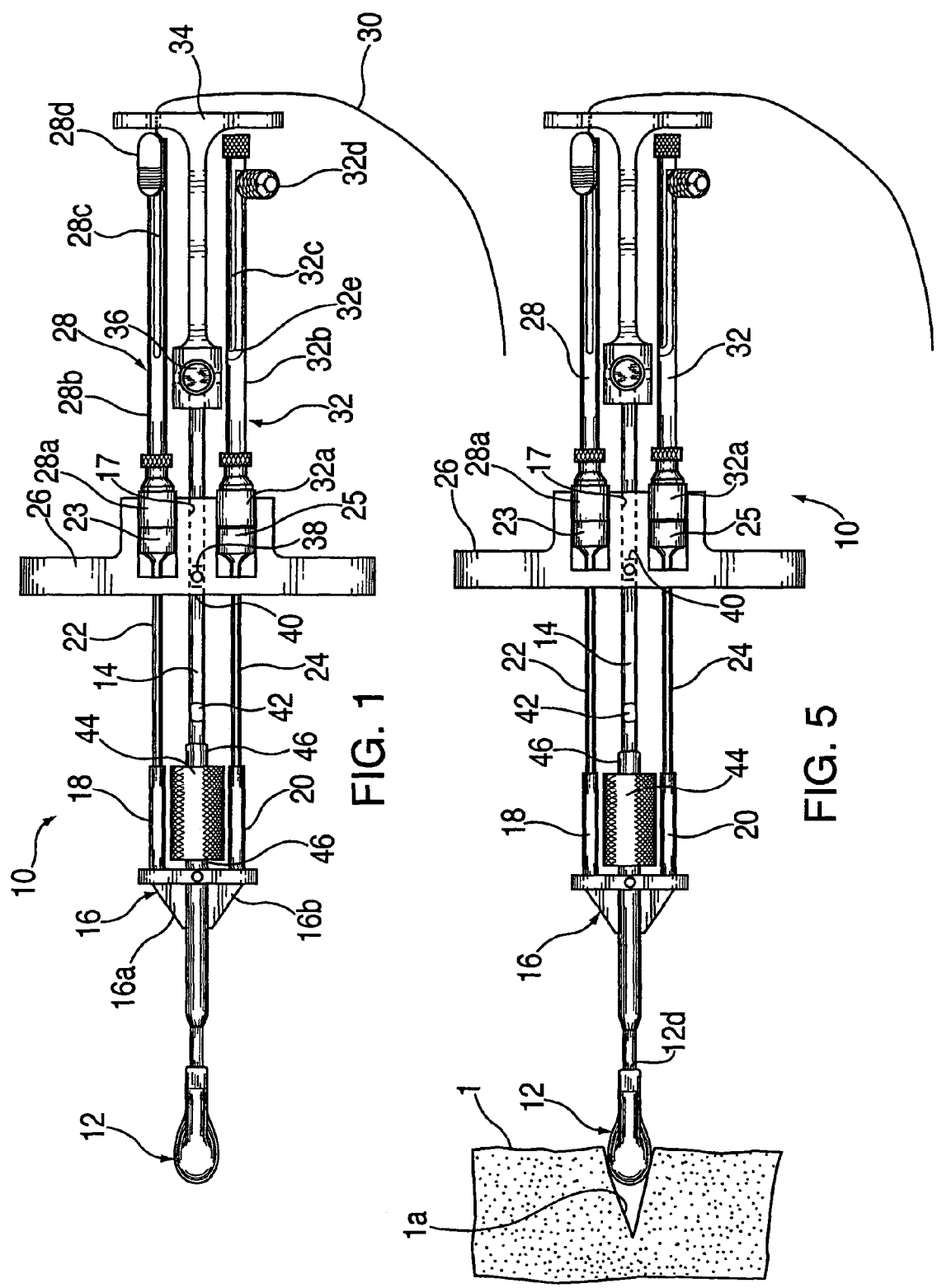

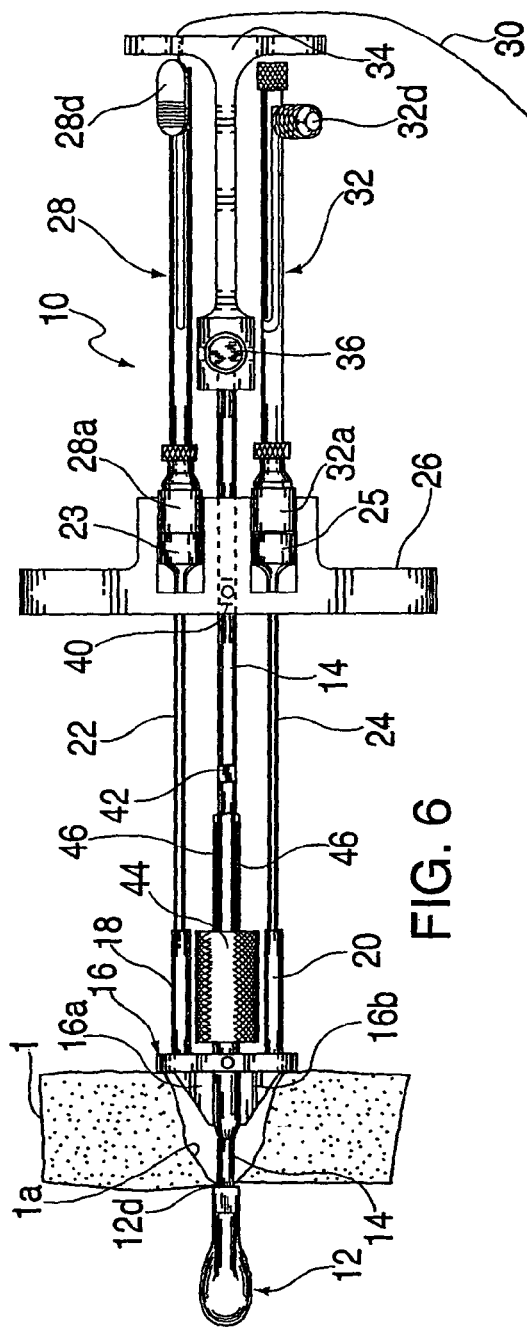
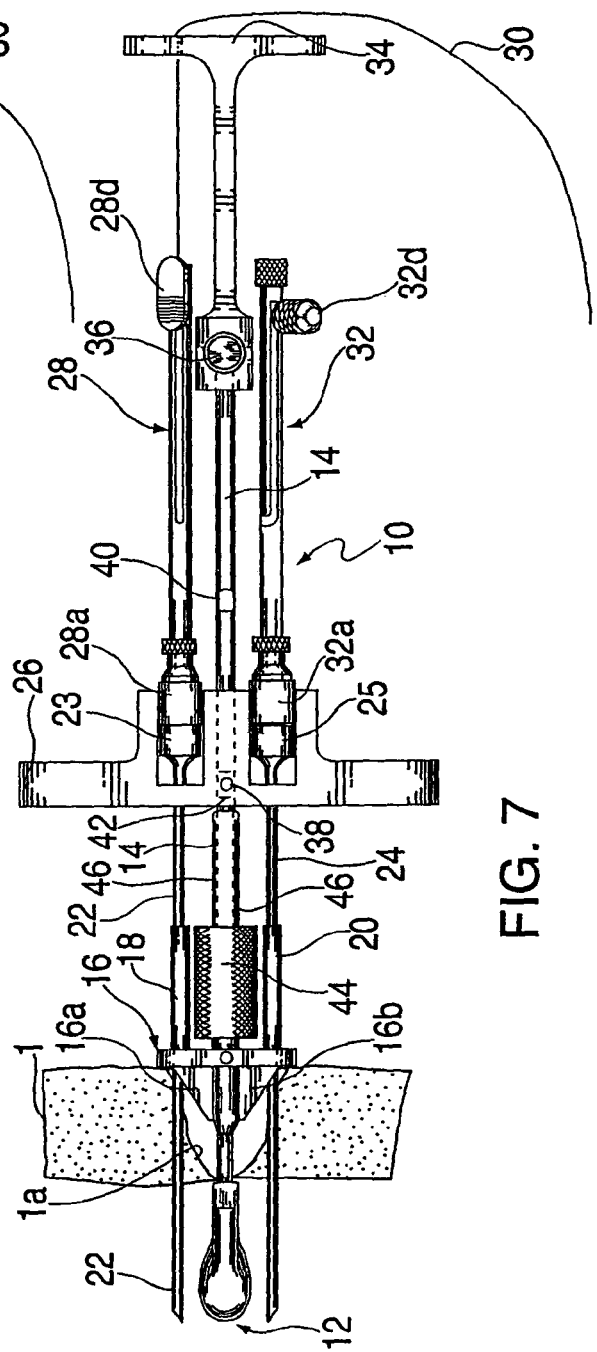

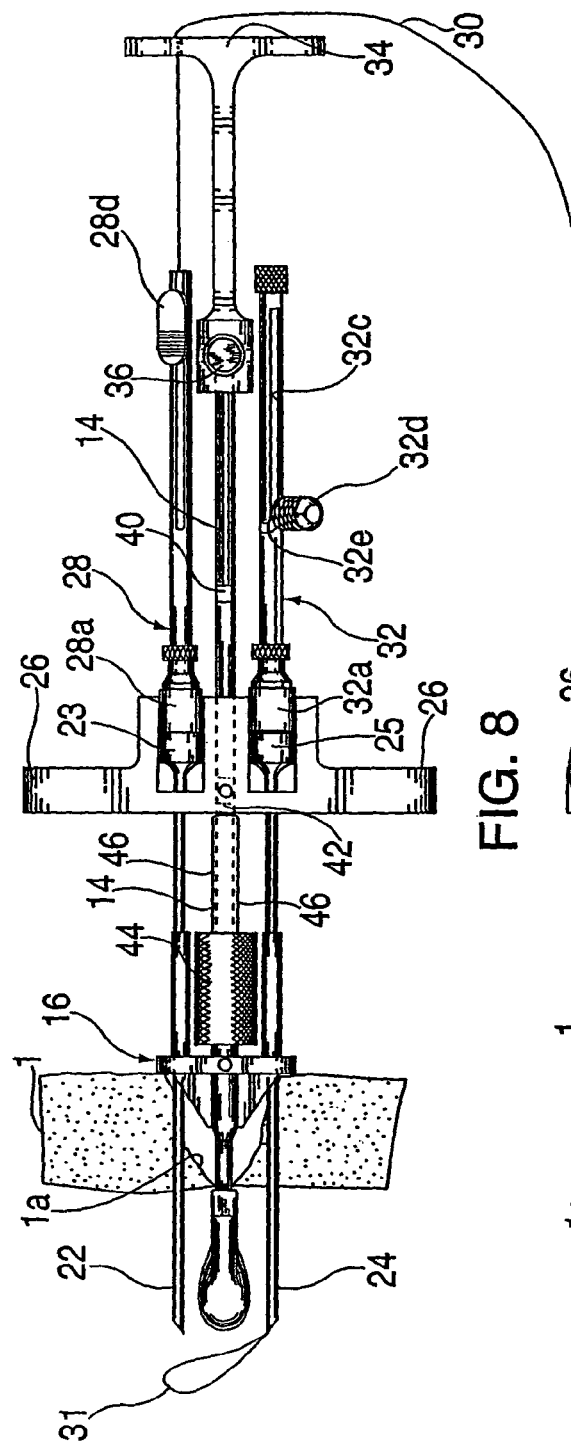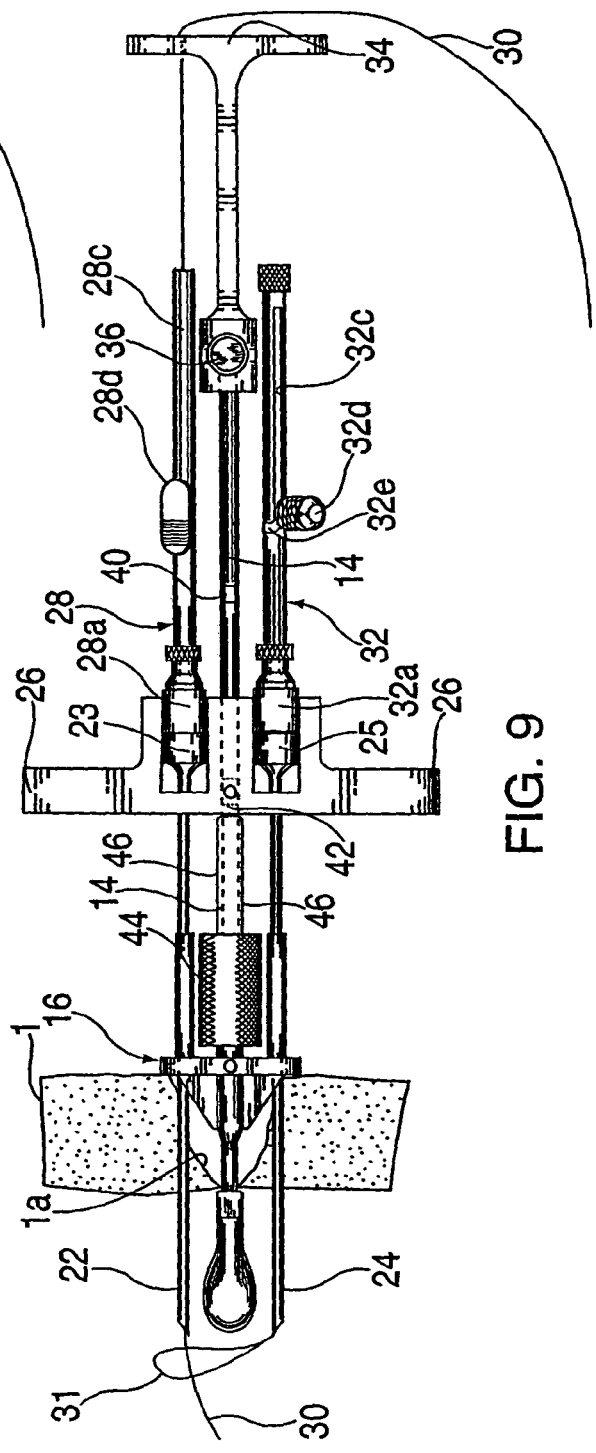

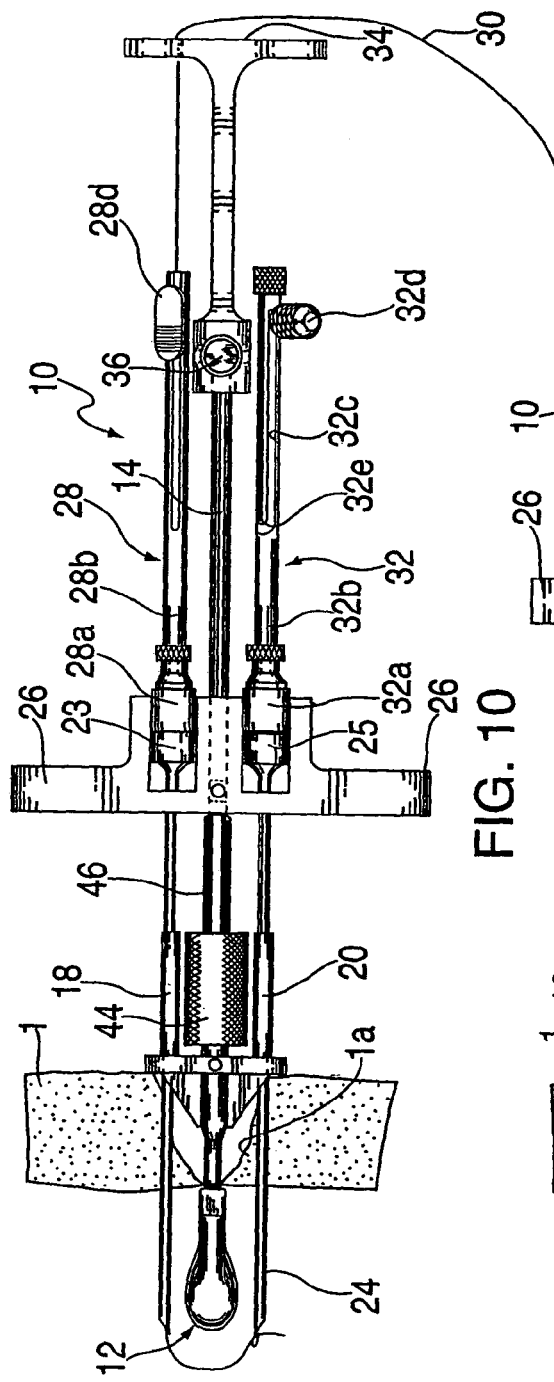
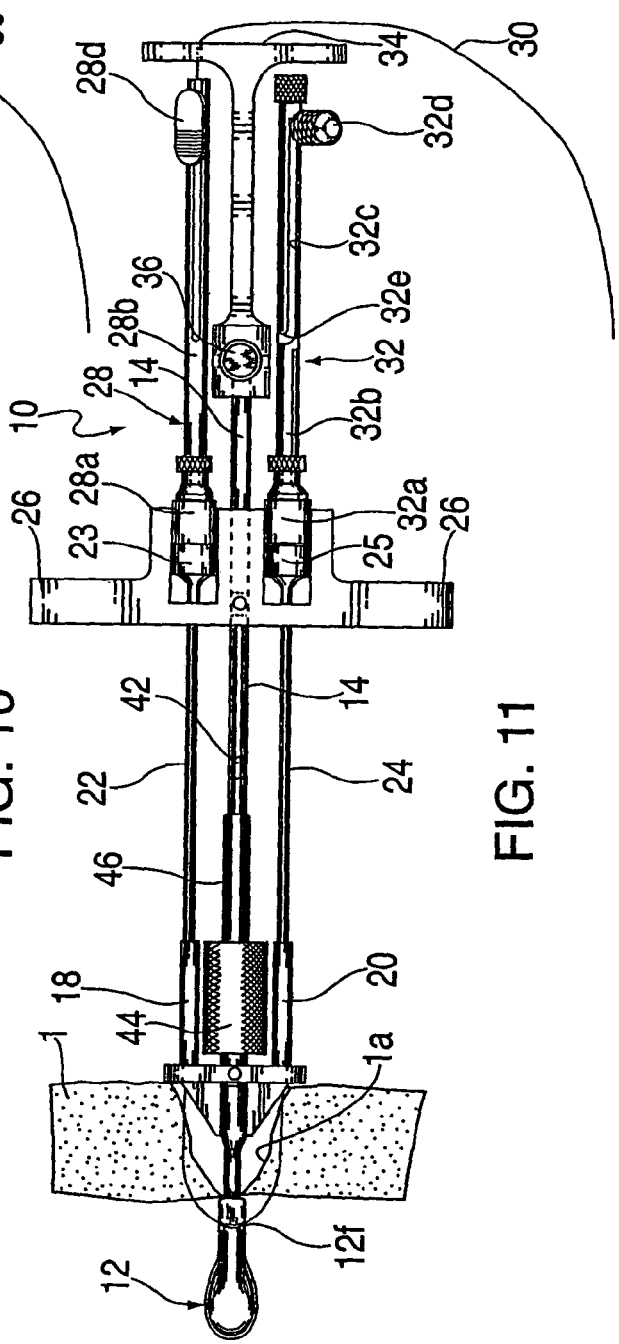
FIG. 10
FIG. 11

METHODS AND INSTRUMENTS FOR CLOSING LAPAROSCOPIC TROCAR PUNCTURE WOUNDS

BACKGROUND OF THE INVENTION

1. Field of the Invention

This invention relates to methods and instruments for suturing puncture wounds and more particularly to instruments for closing trocar puncture wounds formed during endoscopic and laparoscopic surgical procedures.

2. State of the Art

During laparoscopic and endoscopic surgery, one or more small incisions or punctures are made in the patient's body to provide access for one or more tubes or cannula devices. These cannulae, together with the removable puncturing devices which fit into the cannulae, are referred to as trocars. Once extended into the patient's body, the cannulae allow for insertion of various surgical instruments such as scissors, dissectors, retractors, or biopsy instruments together with an endoscope or laparoscope to perform diagnostics and/or surgery. Upon completion of the surgical procedure, the remaining trocar wounds are preferably sutured to close the wound.

Many devices and procedures have been proposed for the efficient and aesthetic closing of trocar wounds. For example, U.S. Pat. No. 5,403,329, issued Apr. 4, 1995 to Hinchcliffe, discloses an instrument for closing trocar puncture wounds having a handle assembly with a stationary portion and a movable portion; an elongated portion attached at a proximal end thereof to the stationary portion of the handle assembly; and needle deploying means associated with the elongated portion. The needle deploying means includes: an actuator member having a proximal end operably connected to the movable portion of the handle assembly and a distal end disposed adjacent a distal end of the elongated portion, the actuator member being slidable between a first position and a second position; and at least one needle carrier member mounted adjacent the distal end of the actuator member, the needle carrier being slidable relative to the actuator member upon movement thereof, between a retracted position substantially within the elongated portion and an extended position substantially without the elongated portion. The instrument also provides a suture retaining feature including at least one elongated channel disposed along the actuator member such that a length of suture may be received and retained within the channel and carried therein, between the elongated portion and the actuator member.

Although the Hinchcliffe device was an improvement over many of the devices prior to it, the Hinchcliffe device still has several disadvantages. One serious disadvantage is that the apparatus is not self-sufficient. It requires the use of forceps or other grasping tools to move needles carrying the suture material.

U.S. Pat. No. 5,462,560, issued Oct. 31, 1995 to Stevens, discloses a double needle ligature device for efficiently creating a loop suture for closing wounds, such as trocar wounds. The device preferably includes a double rod-in-needle assembly to ensure that the suture is positively held in place during needle retraction. Although the Stevens device has some advantages over the Hinchcliffe device, it still has its disadvantages. The suture must be introduced by dragging it into the abdominal cavity alongside the introducing needle. The suture must be manually threaded through the snare loop. The device is unable to secure the wound and maintain pneumoperitoneum. The device is unable to automatically position tissue relative to the needles.

U.S. Pat. No. 5,474,568, issued Dec. 12, 1995 to Scott, discloses a surgical instrument for applying sutures through body tissue including a handle assembly, an elongated housing removably mounted to said handle assembly and having a proximal end portion and a distal end portion, at least one needle carrier operatively mounted in the distal end portion and movable between a retracted position and a deployed position, and a needle releasably retained in the needle carrier member. The instrument may also include a retaining mechanism adapted to retain the at least one needle carrier in the partially deployed position. Although the Scott instrument has the advantage of being able to plug the trocar wound during closure, it has several disadvantages. It can only place a single loop suture. It has no facility for rotating or resetting.

U.S. Pat. No. 5,476,470, issued Dec. 19, 1995 to Fitzgibbons, Jr., discloses a device for suturing closed laparoscopic trocar sites to reduce the incidence of incisional herniation. A pair of needles, hollow and having an eyelet adjacent the pointed end, are secured to a clip which may be fastened over a trocar sheath (cannula). The clip is then forced to slide down the sheath and the two needles penetrate the fascia and underlying muscle surrounding the hole formed by the trocar. The needles may also be spread somewhat after passing within the skin to gain a better bite on the tissue surrounding the trocar sheath. A suture is then threaded down through one hollow needle and passed through the eyelet of the second needle, utilizing the laparoscope and a second accessory sheath. When the device is then withdrawn, the suture remains, passing through the peritoneum, muscle and fascia and may be tightened to close the site upon removal of the sheath. Though interesting in concept, the Fitzgibbons, Jr. device is difficult to operate and can only deploy a single loop of suture.

U.S. Pat. No. 5,573,542, issued Nov. 12, 1996 to Stevens, discloses a surgical tool for endoscopic suture placement which permits a surgeon to place controlled and precise internal ligatures. The tool utilizes a drive rod including an articulating or deflecting portion. When forced to an extended position, the deflecting or articulating portion forms a hook or J-shaped needle, the tip of which can be used to accurately position the suture. Although the Stevens device may be useful in some applications, it does not automatically deploy a suture, it merely aids in its deployment.

U.S. Pat. No. 5,591,180, issued Jan. 7, 1997 to Hinchcliffe, discloses an apparatus for suturing body tissue comprising first and second elongated body halves detachably connected to one another and first and second needles movable with respect to the first and second body halves. Each of the needles has a penetrating tip facing in a distal direction. At least one actuator is provided which is operatively associated with each of the first and second needles, wherein actuation of the at least one actuator advances the first and second needles into body tissue. The needles are advanced through the body tissue positioned in the window formed in each of the body halves to engage a ferrule having a suture connected thereto.

U.S. Pat. No. 5,722,981, issued Mar. 3, 1998 to Stevens, discloses a double needle ligature device for efficiently creating a loop suture for closing wounds, such as trocar wounds. The device preferably includes a double needle assembly to ensure that the suture is positively held in place during needle retraction. This patent improves upon Stevens' earlier device in that the suture is carried inside a hollow needle rather than alongside a needle. However, it still suffers from the other disadvantages of Stevens' earlier two-needle device.

SUMMARY OF THE INVENTION

It is therefore an object of the invention to provide methods and apparatus for closing trocar puncture wounds.

It is another object of the invention to provide an apparatus for placing a loop suture that engages the inner layers of the abdominal wall but not the skin and the outer layers.

It is still another object of the invention to provide an apparatus for quickly and accurately suturing trocar puncture wounds.

It is yet another object of the invention to provide an apparatus which functions automatically with a minimum of user input.

In accord with these and other objects which will be discussed in detail below, the apparatus of the present invention includes an obturator coupled to a central shaft and a coaxially disposed skin pressure plate. The obturator and skin pressure plate are movable relative to each other. The skin pressure plate is provided with two spaced apart needle guides. A pair of hollow needles, held in the guides of the pressure plate are coupled to a needle mounting plate which is movable over the central shaft. One of the needles is provided with a suture control mechanism for moving a suture through the needle and the other needle is provided with a snare control mechanism for moving a snare through the needle. The central shaft is preferably coupled to a handle and is preferably provided with detents which are engaged by the needle mounting plate. The skin pressure plate is preferably coupled to the central shaft with a collar which clamps onto the central shaft by means of a split threaded clamp mechanism.

Methods for using the apparatus of the invention include starting with the needles and the skin pressure plate fully retracted, placing the obturator through the puncture wound, advancing and securing the skin pressure plate, and extending the pair of needles. With the needles extended, the snare is advanced through one needle and then the suture is advanced through the other needle and into the snare. The snare is withdrawn, capturing the suture and holding it against the tip of the needle. The needles are retracted and the apparatus is removed from the body. The suture is released and tied. The suturing procedure may then be repeated.

Additional objects and advantages of the invention will become apparent to those skilled in the art upon reference to the detailed description taken in conjunction with the provided figures.

BRIEF DESCRIPTION OF THE DRAWING

FIG. 1 is a side elevation view of the apparatus of the invention in its configuration prior to use;

FIG. 5 is a view similar to FIG. 1 illustrating a first step in operating the apparatus of the invention;

FIG. 6 is a view similar to FIG. 1 illustrating a second step in operating the apparatus of the invention;

FIG. 7 is a view similar to FIG. 1 illustrating a third step in operating the apparatus of the invention;

FIG. 8 is a view similar to FIG. 1 illustrating a fourth step in operating the apparatus of the invention;

FIG. 9 is a view similar to FIG. 1 illustrating a fifth step in operating the apparatus of the invention;

FIG. 10 is a view similar to FIG. 1 illustrating a sixth step in operating the apparatus of the invention;

FIG. 11 is a view similar to FIG. 1 illustrating a seventh step in operating the apparatus of the invention.

DETAILED DESCRIPTION OF THE PREFERRED EMBODIMENTS

Figure 4:
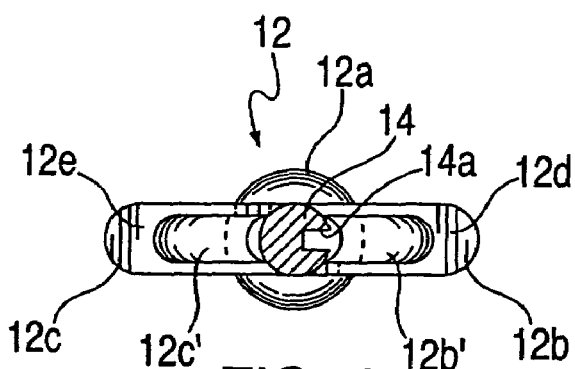
FIG. 4 is an end view of the obturator.

Turning now to FIG. 1, a suturing apparatus 10 according to the invention includes an obturator 12 coupled to the distal end of a central shaft 14 and a coaxially disposed skin pressure plate 16. As used herein, distal means farthest from the practitioner and closest to the surgical site. Proximal means closest to the practitioner. The obturator 12 and skin pressure plate 16 are movable relative to each other. The skin pressure plate 16 is provided with two spaced apart needle guides 18, 20. A pair of hollow needles 22, 24, held in the guides 18, 20 of the pressure plate 16 are coupled to a needle mounting plate 26 which is movable over the central shaft. One of the needles is provided with a suture control mechanism 28 for moving a suture 30 through the needle 22 and the other needle 24 is provided with a snare control mechanism 32 for moving a snare 31 (FIG. 7) through the needle 24 as described in more detail below.

The proximal end of the central shaft 14 is preferably coupled to a handle 34 by a set screw 36. The needle mounting plate 26 is preferably provided with a biased pin 38 which alternately engages detents 40, 42 on the central shaft 14. The skin pressure plate 16 has a central bore 17 and is preferably coupled to the central shaft via knurled locking nut 44 threadably received on a threaded split collar 46 centrally mounted on skin pressure plate 16 about central bore 17 so as to be co-axially arranged with central bore (not shown) and mounted on central shaft 14. Locking nut 44 tightens the split collar 46 against shaft 14 thereby fixing the skin pressure plate 16 to central shaft 14. The skin pressure plate has two skin stretching fins 16a, 16b which are described in more detail below with reference to FIGS. 6-11.

The suture control mechanism 28 is mounted onto the hub 23 of needle 22 by way of a conventional Luer lock 28a. The suture control 28 includes a sleeve 28b having a guiding slot 28c and a finger slide 28d. The finger slide 28d is coupled to the suture 30 as described in more detail below and is preferably biased to the proximal position shown by a spring (not shown). When the finger slide 28d is depressed, it is moved distally by manual control moving a pre-measured length of suture through the end of needle 22. The spring returns the finger slide to its starting position.

The snare control mechanism 32 is mounted onto the hub 25 of the needle 24 by way of a conventional luer lock fitting 32a. The snare control includes a sleeve 32b having a guiding slot 32c and a sliding pin 32d. The pin 32d is coupled to a snare (shown and described in more detail below with reference to FIGS. 8-12) and is movable along the slot 32c. The pin 32d is biased proximally, i.e., to the position shown in FIG. 1 by a spring (not shown). The distal end of the slot 32c is provided with a stop 32e to hold the pin 32d when pressed forward and rotated. When pressed forward and rotated into the stop 32e, the pin 32d delivers the snare through the needle 24 to the appropriate capture position.

Figure 3:
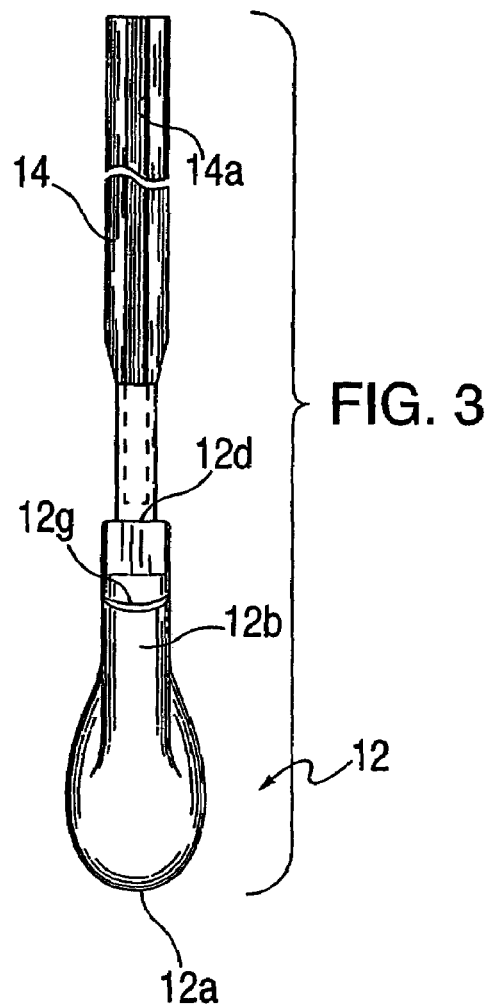
FIG. 3 is an enlarged broken side view of the obturator.
Figure 2:
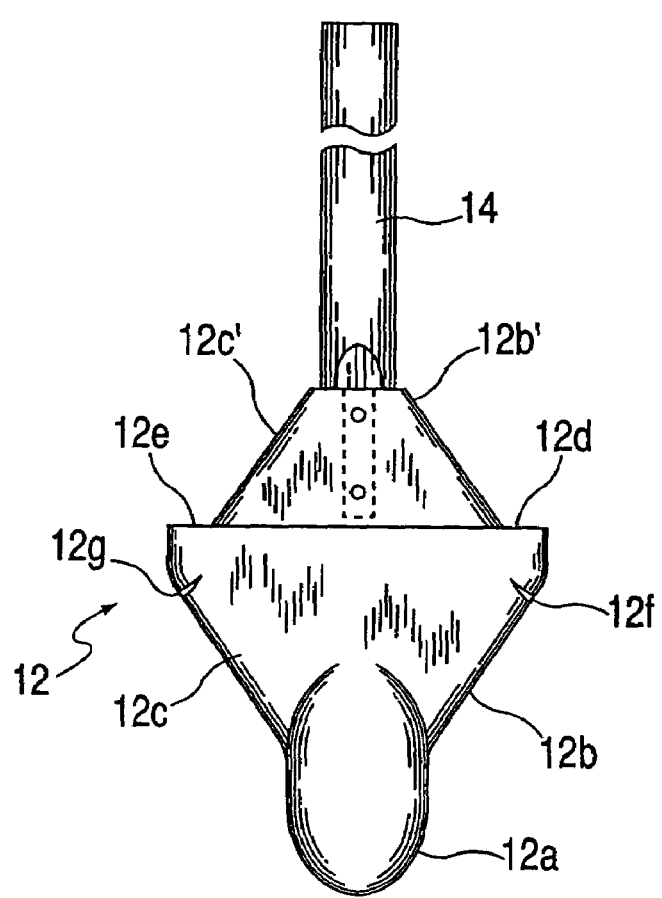
FIG. 2 is an enlarged broken top view of the obturator.

Turning now to FIGS. 2-4, the obturator 12 is a small, sculpted mass which is designed to be placed into and through the puncture wound 1a in the abdominal wall that remains after a laparoscopic trocar is removed. In particular, the obturator 12 has a bulbous tip 12a and a pair of proximally flared spreading fins 12b, 12c, 12b', 12c'. The fins terminate in fascia supporting shelves 12d, 12e. Suture capturing notches 12f, 12g are present on fins 12b and 12c to control the position of the suture during removal of the device.

As described in more detail below with reference to FIGS. 5-7, the dimensions and shape of the obturator 12 permit it to pass through the wound easily with a minimum of effort. Once introduced, gentle retraction on the obturator 12 allows the fascia spreading fins 12b', 12c' to increase the tension and change the shape of the wound. The fascia supporting shelves 12d, 12e allow upward tension to be applied to the fascia to resist the pressure applied by the needles during their entry.

As seen best in FIGS. 3 and 4, the central shaft 14 is provided with an alignment groove 14a which is engaged by the movable components so that the components remain angularly disposed in the correct manner relative to each other.

FIGS. 5-12 illustrate the methods for using the apparatus 10 of the invention as well as additional features of the invention mentioned briefly above.

Starting with the needles 22, 24 and the skin pressure plate 16 fully retracted to their proximal most position, the obturator 12 is inserted in the puncture wound 1a, as shown in FIG. 5. As mentioned above, the fins 12b', 12c' of the obturator result in the linear stretching of the round or irregular wound that is to be closed. This stretching permits the needles 22, 24 to engage the inner layers of the abdominal wall properly. In particular, the needles penetrate the fascia and peritoneum of the abdominal wall, The tightened tissues allow the needles to be passed through them and change the shape of the wound from a round or irregular hole to a stretched linear defect so that an adequate amount of the tissue can be engaged by the needles.

As shown in FIG. 6, after the obturator 12 is installed, the skin pressure plate 16 is advanced by moving the pressure plate 16 along the shaft 14 and is secured by tightening the knurled locking nut 44. As the locking nut 44 is rotated it pinches the split collar 46 against the shaft 14, and locks the pressure plate in position. As mentioned above, the skin pressure plate 16 has a pair of skin stretching fins 16a, 16b which are substantially orthogonal to the fins on the obturator 12 and which guide the proper alignment of the device 10 relative to the skin 1 and skin incision 1a. Also, the fins 16a, 16b stretch the skin incision 1a and allow the needle guide apertures 18, 20 to be positioned within the soft tissue of the wound 1a. It is important that the needles 22, 24 do not engage the outer surface of the body wall, i.e., skin 1, when they are inserted. The type of needles used will not penetrate the skin easily and a properly placed suture should only include the two deepest layers of the abdominal wall, the fascia and peritoneum. The needle guides 18, 20 run along the edge of the skin stretching fins 16a, 16b. These guides 18, 20 store and guide the needles 22, 24 during their movements as well as hiding the sharp tips of the needles when retracted.

Referring now to FIGS. 6 and 7, with the obturator 12 and the skin pressure plate 16 in place, the needle mounting plate 26 is moved distally until it engages the second detent 42 on the central shaft 14. This advances the needles 22, 24 through the body wall until the ends of the needles 22, 24 are approximately even with the tip of the obturator 12 (FIG. 7).

Turning now to FIG. 8, with the needles 22, 24 now extended, the pin 32d of the snare control mechanism 32 is moved distally against the spring (not shown) through the slot 32c and rotated into the stop 32e. This advances the snare 31 through needle 24 and rotates it to the proper position relative to needle 22.

The relationship between the snare 31 and the snare control mechanism 32 is predetermined so that the snare protrudes the correct distance and rotates through the correct arc each time the pin 32d is pushed to the end of the slot 32c and rotated into the lock 32e.

With the snare 31 now in place, the suture 30 is delivered as shown in FIG. 9. In particular, the finger slide 28d is manually advanced through the slot 28c against the action of the spring (not shown). The suture control mechanism 28 works in synchrony with the snare control mechanism 32 to enable the passage of the suture 30 through the tissue engaged by the needles 22, 24.

Prior to use, the suture 30 is pre-positioned in the suture control mechanism 28 so that the suture material extends to just within the tip of the needle 22. Once the device is properly positioned and the snare 31 is in the proper position, the suture control mechanism 28 is advanced and the suture 30 is automatically inserted through the needle 22 and into the waiting snare 31 as shown in FIG. 9.

After the suture is inserted by the suture control mechanism 28, the snare collar pin 32d is manually tripped out of the lock 32e and is automatically retracted back along slot 32c by the spring (not shown) to capture the suture 30 with the snare 31 in the needle 24 as shown in FIG. 10. The needles 22, 24 are then pulled back as shown in FIG. 11 and the suture 30 is caught by one of the suture capturing notches, 12f, 12g.

Figure 12:
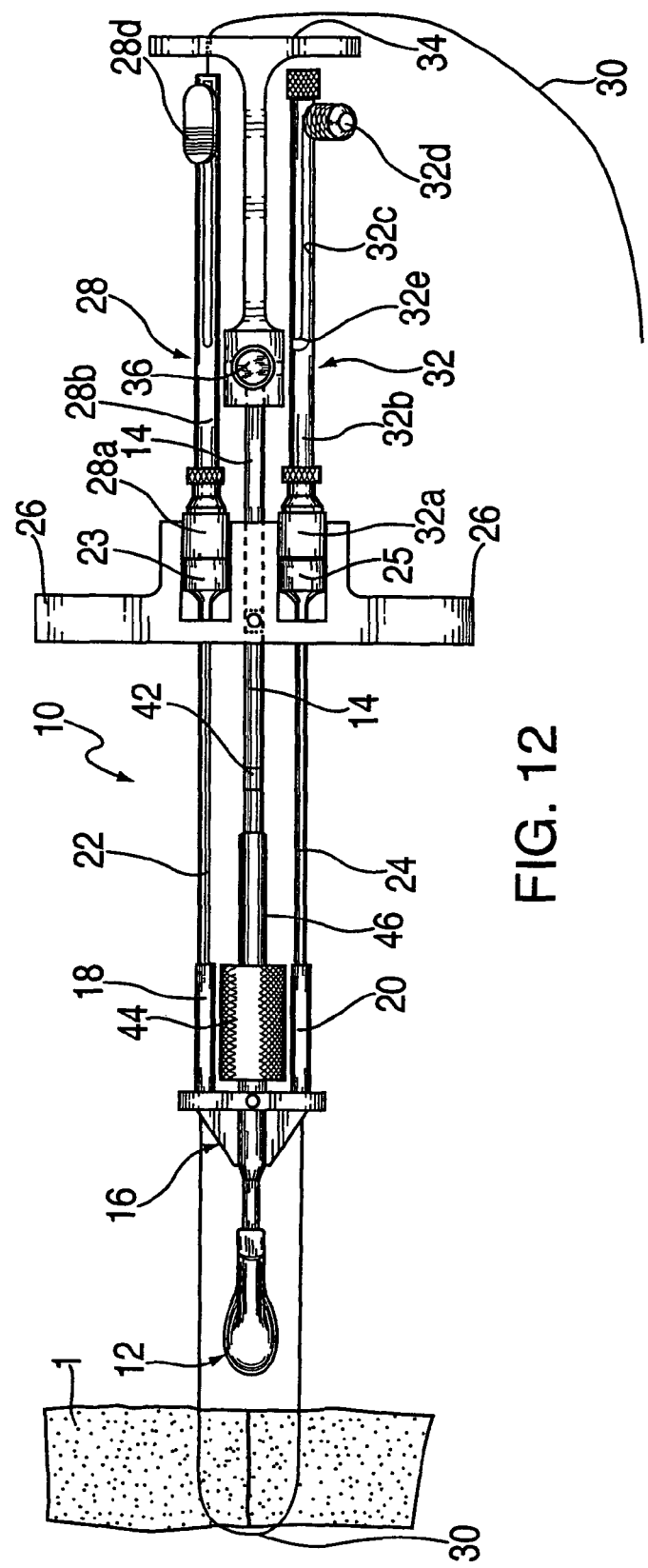
FIG. 12 is a view similar to FIG. 1 illustrating an eighth step in operating the apparatus of the invention.

After the device 10 is removed from the patient as shown in FIG. 12, the suture 30 is pulled out of its locked condition by a gentle pulling motion at the snare end, is cut at the suture needle end, and is then tied (not shown). The procedure may be repeated as necessary.

Although not essential to the invention, according to the presently preferred embodiment, the handle 34 facilitates gross movements of the device and is attached to the central shaft by way of a thumbscrew 36 that fits into a cut-out on the central shaft 14. A suture storage reel (not shown) can be built into the handle and holds enough suture for several wound closures.

Also according to the presently preferred embodiment, the needles 22, 24 are 16 gauge 4 inch Hustead epidural needles which are fitted into the needle mounting plate 26 and pass through the skin pressure plate 16 to facilitate the correct placement of the suture 30. These needles are standard surgical instruments and are not modified prior to their use. The curved tips of the needles are intended to pass through the tissue without becoming impacted with fatty material and will also reduce the risk of injury to the abdominal viscera if inadvertent contact occurs. The hub of each needle has flat surfaces that fits into the needle mounting plate 26 and accepts a set screw (not shown).

The preferred suture is the string-like material that is positioned by the device in such a way that the structural elements of the abdominal wall are securely approximated once the suture is tied using standard surgical techniques. A variety of suture materials may function properly and be suitable for use with the invention. An example of a suture material with the desirable physical characteristics in terms of strength and flexibility is O Prolene (polypropylene)

manufactured by Ethicon. The suture is fed off a reel which holds approximately 48 inches of suture material, enough to place four separate suture loops. The suture is grasped by hand as the device is removed from the body cavity and cut-off using a standard surgical suture scissors at approximately 12 inches of length. By cutting the suture at the exit point of the suture needle, with the slide in the proximal position, the suture control mechanism is in the start position for repeated use.

There have been described and illustrated herein methods and instruments for suturing the wound caused by a trocar in laparoscopic or endoscopic surgery. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

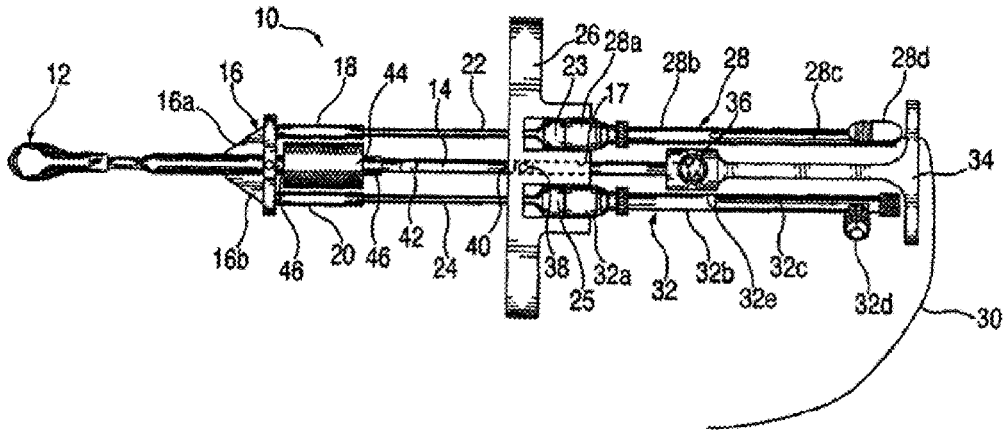

The invention claimed is:

1. An apparatus for applying a suture to a wound, comprising:
    a) a central shaft having a proximal end and a distal end;
    b) an obturator coupled to the distal end of said shaft;
    c) a pair of hollow needles slidably coupled to said central shaft, each of said needles having a sharp end and being movable from a first position where said sharp ends are distant from said obturator to a second position where said sharp ends are close to said obturator;
    d) a suture control mechanism coupled to one of said needles for delivering suture material through the sharp end of the needle;
    e) a snare control mechanism coupled to the other of said needles for delivering a snare through the sharp end of the needle;
    f) a skin pressure plate mounted on said shaft and movable relative to said obturator;
    g) a needle mounting plate mounted to said central shaft; and
    h) said skin pressure plate having a threaded split collar coaxially disposed on said central shaft and a rotatable locking nut, wherein said rotatable locking nut is threadably received on said split collar of said skin pressure plate and, upon tightening, locks said skin pressure plate to said central shaft.

2. An apparatus according to claim 1, wherein:
said obturator has a bulbous distal end and a pair of fascia stretching fins.

3. An apparatus according to claim 2, wherein:
said fascia stretching fins taper proximally.

4. An apparatus according to claim 2, wherein:
said fascia stretching fins terminate in a fascia supporting shelf.

5. An apparatus according to claim 1, wherein:
said skin pressure plate has a pair of skin stretching fins.

6. An apparatus according to claim 5, wherein:
said fins taper distally.

7. An apparatus according to claim 5, wherein:
the sharp ends of said needles pass through said fins.

* * * * *

UNITED STATES PATENT AND TRADEMARK OFFICE
CERTIFICATE OF CORRECTION

PATENT NO. : 7,320,693 B2
APPLICATION NO. : 10/645405
DATED : January 22, 2008
INVENTOR(S) : Pollak et al.

It is certified that error appears in the above-identified patent and that said Letters Patent is hereby corrected as shown below:

On the title page: should be deleted
Item (12 & 76) should read item -- (12) Pollak -- and item -- (76) Stanley B. Pollak, -- therefore the attached title page.

Signed and Sealed this

Fifth Day of August, 2008

JON W. DUDAS
*Director of the United States Patent and Trademark Office*

(12) United States Patent
Pollak et al.

(10) Patent No.: US 7,320,693 B2
(45) Date of Patent: Jan. 22, 2008

(54) METHODS AND INSTRUMENTS FOR CLOSING LAPAROSCOPIC TROCAR PUNCTURE WOUNDS

(76) Inventors: Stanley B. Pollak, 71 Forest Ave., Nesconset, NY (US) 11767; Anthony D. Castabile, P.O. Box 2097, Setauket, NY (US) 11733

(*) Notice: Subject to any disclaimer, the term of this patent is extended or adjusted under 35 U.S.C. 154(b) by 854 days.

(21) Appl. No.: 10/645,405

(22) Filed: Aug. 21, 2003

(65) Prior Publication Data
US 2005/0043746 A1 Feb. 24, 2005

(51) Int. Cl.
*A61B 17/04* (2006.01)
(52) U.S. Cl. .................................. 606/144
(58) Field of Classification Search ........ 606/144–148, 606/150, 215, 221, 220, 232, 139, 213; 289/10, 289/17
See application file for complete search history.

(56) References Cited

U.S. PATENT DOCUMENTS

| | | | |
|---|---|---|---|
| 4,779,616 A | 10/1988 | Johnson | |
| 5,195,505 A | 3/1993 | Josefsen | |
| 5,330,488 A | 7/1994 | Goldrath | |
| 5,364,410 A | 11/1994 | Failla et al. | |
| 5,391,182 A | 2/1995 | Chin | |
| 5,437,681 A | 8/1995 | Meade et al. | |
| 5,439,469 A | 8/1995 | Heaven et al. | |
| 5,462,560 A | 10/1995 | Stevens | |
| 5,474,568 A | 12/1995 | Scott | |
| 5,476,470 A | 12/1995 | Fitzgibbons, Jr. | |
| 5,503,634 A | 4/1996 | Christy | |
| 5,562,688 A | 10/1996 | Riza | |
| 5,591,180 A | 1/1997 | Hinchliffe | |
| 5,697,889 A | 12/1997 | Slotman et al. | |
| 5,716,369 A | 2/1998 | Riza | |
| 5,722,981 A * | 3/1998 | Stevens | 606/148 |
| 5,741,277 A | 4/1998 | Gordon et al. | |
| 5,830,233 A | 11/1998 | Basson | |
| 5,836,956 A | 11/1998 | Buelna et al. | |
| 5,954,734 A * | 9/1999 | Thomason et al. | 606/148 |
| 5,984,948 A * | 11/1999 | Hasson | 606/213 |
| 5,993,466 A | 11/1999 | Yoon | |
| 6,152,936 A | 11/2000 | Christy et al. | |
| 6,245,080 B1 * | 6/2001 | Levinson | 606/144 |

* cited by examiner

*Primary Examiner*—Anhtuan T. Nguyen
*Assistant Examiner*—Tuan Van Nguyen
(74) *Attorney, Agent, or Firm*—Galgano & Associates, PLLC

(57) ABSTRACT

An instrument for applying a suture to a trocar wound includes an obturator coupled to a central shaft and a coaxially disposed skin pressure plate. The obturator and skin pressure plate are movable relative to each other, and function together to position the tissue and needles relative to each other. The skin pressure plate is provided with two spaced apart needle guides. A pair of hollow needles, held in the guides of the pressure plate are coupled to a needle mounting plate which is movable over the central shaft. One of the needles is provided with a suture control mechanism for moving a suture through the needle and the other needle is provided with a snare control mechanism for moving a snare through the needle.

7 Claims, 6 Drawing Sheets